United States Patent [19]

Bonniaud et al.

[11] Patent Number: 5,311,782
[45] Date of Patent: May 17, 1994

[54] PROCESS AND APPARATUS FOR THE AUTOMATIC REMOVAL OF A MATERIAL SAMPLE DURING ITS POURING INTO A CONTAINER

[75] Inventors: Roger Bonniaud, Bagnols sur Cée; Antoine Jouan, Villeneuve les Avignon; Jean-Pierre Moncouyoux, Bagnols sur Céze; Michel Saint-Gaudens, Laudun, all of France

[73] Assignee: Commissariat a l'Energie Atomique, Paris, France

[21] Appl. No.: 806,000

[22] Filed: Dec. 9, 1991

[30] Foreign Application Priority Data

Dec. 12, 1990 [FR] France ............... 90 15567

[51] Int. Cl.⁵ .................. G01N 1/10; G01N 33/38; G21F 9/00
[52] U.S. Cl. .................. 73/863.53; 73/864.53
[58] Field of Search ........... 73/863.53, 863.54, 863.55, 73/864.53, 864.59, DIG. 9

[56] References Cited

U.S. PATENT DOCUMENTS

| | | | |
|---|---|---|---|
| 1,362,968 | 12/1920 | Stewart | 73/863.55 |
| 1,414,726 | 5/1922 | Delamater | 73/863.55 |
| 3,122,019 | 2/1964 | Wellenius et al. | 73/863.55 |
| 3,295,171 | 1/1967 | Strange et al. | 73/DIG. 9 |
| 3,365,953 | 1/1968 | Gold et al. | 73/864.62 |
| 3,387,497 | 6/1968 | Huntington | 73/863.54 |
| 4,389,906 | 6/1983 | Bartholomay | 73/863.55 |
| 4,597,562 | 7/1986 | Joyce | 254/334 |
| 5,060,530 | 10/1991 | Haughton | 73/864.53 |

FOREIGN PATENT DOCUMENTS

| | | | |
|---|---|---|---|
| 0728668 | 10/1942 | Fed. Rep. of Germany | 73/863.53 |
| 363858 | 8/1906 | France . | |
| 219740 | 1/1990 | Japan . | |
| 0363891 | 3/1973 | U.S.S.R. | 73/863.54 |
| 1341555 | 12/1973 | United Kingdom . | |
| 2034667A | 6/1980 | United Kingdom | 73/863.53 |

Primary Examiner—Hezron E. Williams
Assistant Examiner—George Dombroske
Attorney, Agent, or Firm—Michael N. Meller

[57] ABSTRACT

The invention permits the automatic removal of a liquid sample without human intervention. The sample is removed during the pouring of liquid glass into its container. Use is made of a bucket fitted at the end of an oscillating arm. The mechanism is controlled by a fusible or meltable pellet, which melts when the glass level rises in the container. A prestressed spring and a counterweight enables the arm to pass from an initial position into a sampling position and then to a folded back position. The invention also provides an apparatus for raising the bucket and an apparatus for recovering the solidified sample in said bucket. The invention is used for taking a radioactive glass sample having to be permanently stored in a container.

8 Claims, 6 Drawing Sheets

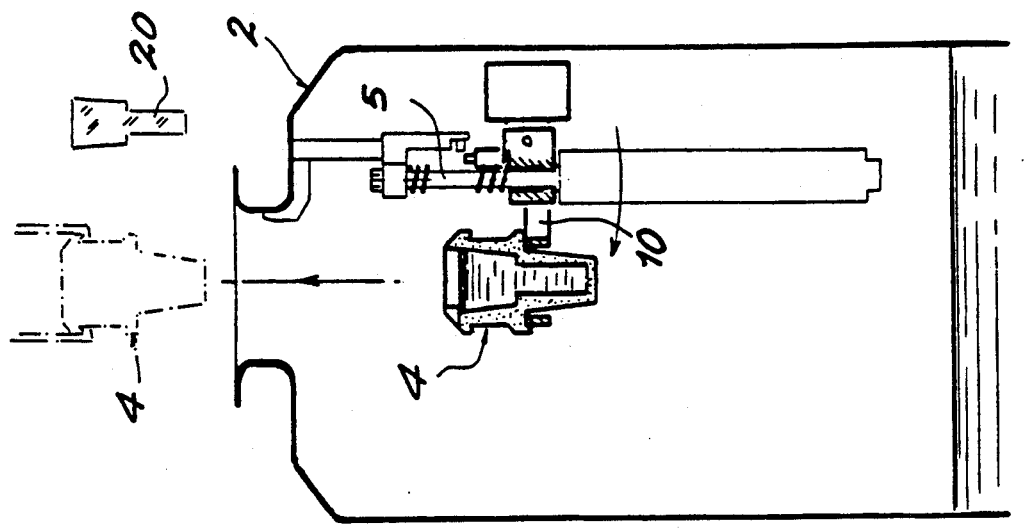
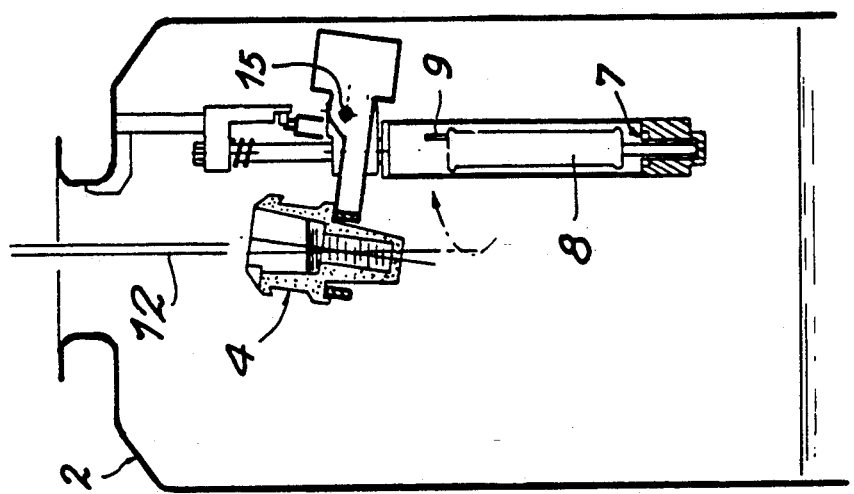
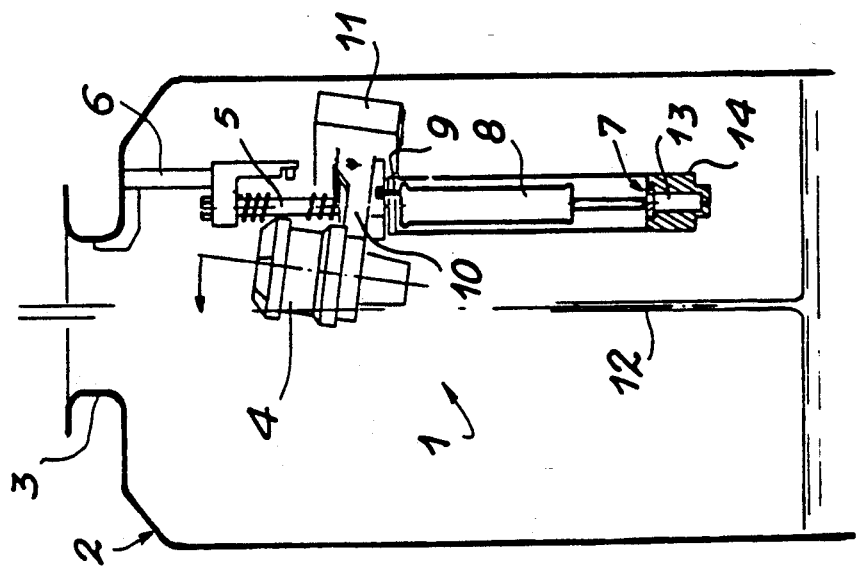

PROCESS AND APPARATUS FOR THE AUTOMATIC REMOVAL OF A MATERIAL SAMPLE DURING ITS POURING INTO A CONTAINER

DESCRIPTION

1. Field of the Invention

The invention relates to the entirely automated removal of a material sample to be placed in a container, when no apparatus has been provided for this purpose in the container or in the installations for treating the said material prior to its pouring into the container. In the nuclear industry, it more particularly relates to solutions of fission products having to be definitively stored in glass form. The invention applies in general terms to the removal of a liquid or molten material sample during its pouring into the container, whose interior is inaccessible for an operator.

2. Prior Art

The use of nuclear reactors involves the permanent storage of spent fission products. The latter include solutions of products and radioactive waste that are vitrified with a view to their permanent storage. The final phase of said vitrification generally consists of pouring the solution into its storage container.

The quality of the glass to be stored must be warranted by the monitoring of numerous operating parameters. Reference is e.g. made to the chemical composition of the solutions to be vitrified, the material balances, all the technological parameters controlling the process, the refining time, etc. Possible fluctuations in these parameters on either side of the nominal reference values are limited and defined by upper and lower limits, so that the composition of the product always remains within an acceptably range. The latter is determined by laboratory sensitivity studies and confirmed by technological experiments.

Normally this principle is qualified by tests performed on an inactive prototype. Nevertheless, safety and security organizations, in this case ANDRA, often require an active verification by direct inspection of the product quality. This inspection can take place in a sequential manner, or can be required whenever significant variations in the operating parameters justify it.

Consequently, an inspection requires the removal of a glass sample. Such an operation is not easy in an industrial operation for the following reasons. The access to the removal point is generally limited and often cannot be directly seen, whilst being relatively inaccessible to telemanipulators. Moreover, the use of remotely controlled means is not always desirable during operation, due to the presence of induction currents, high voltages and high current intensities. The pouring of the glass to be vitrified generally takes place under unfavourable thermal conditions. A maximum sealing is required between the container and the glass production furnace in order to limit the entrainment by volatility of radioactive compounds and thus prevent external contamination of the container. Any sample removal system which breaks this seal cannot be used in this case. Under these conditions, the glass sampling apparatuses must be integrated into the production furnace or into the container.

Different sample removal apparatuses are known or used.

A first type of apparatus involves the direct removal of a solid cooled glass sample from the container. This sampling is brought about by coring the glass directly in the container using a diamond tool and a wedge device, thus making it possible to break the core at the end of cutting. Such an apparatus has the advantage of removing the glass outside the actual pouring operations, but still suffers from the following disadvantages. The apparatus is complex and requires a specific working cell. Coring takes place on the surface and is consequently only representative of the glass at the end of pouring. The operation must take place under water, so that the sample will be deteriorated by leeching lixiviation. In this case, the sample surface is abraded and is consequently not very representative of the true surface state. Moreover, the upper level of the glass in a container is often fractured. Consequently the obtaining of a one-piece core is of an arbitrary nature.

A second type of sample removal involves carrying out the latter in the melting furnace. The operation can take place by suction using a rod immersed in the molten glass. The main disadvantage of this system is its complexity and its inadequate performance.

Sample removal can also take place during pouring and in this case between the production furnace and the crucible is placed, level with the connecting tube, an apparatus representing a graphite mould beneath the glass stream. For example, for this purpose a rotary means has been constructed, which carries three graphite crucibles arranged at 120° from one another and its operation is possible by a predetermined rotation plan. In addition, a translation sampling apparatus is known, in which a jack brings a graphite mould beneath the stream. These apparatuses make it possible to remove several samples during each pouring or casting operation and at several filling levels of the container. However, considerable costs are involved, which are only justified when a large number of samples have to be taken. Such apparatuses must also be incorporated at the time of furnace design. Moreover, the sample cools very rapidly and generally leads to a fracturing of the latter and avoids the evolution of the possible crystallization. Under these conditions, the sample does not always represent the state of the glass in the container. A controlled cooling device can obviate this disadvantage, but it increases complexity, e.g. involving a gradient furnace simulating the cooling conditions of the real glass.

All these apparatuses can provide a satisfactory solution if provided at the time of designing the installation and in particular the furnace and provided that their installation is justified by an adequate number of samples being taken.

SUMMARY OF THE INVENTION

The object of the present invention is to obviate this disadvantage by proposing a process and apparatuses for removing a sample and be able to adapt to the already existing radioactive glass storage and vitrification equipment. In this case, the objective of the sample removal is often direct vitrification and the monitoring of the operating parameters. When sampling takes place in the container, it avoids the risks associated with the complexity of an apparatus integrated into the melting furnace.

To this end, the first main object of the invention is a process for the automatic removal of a material sample, which is at least instantaneously in the liquid or molten phase and which can be poured into a container and which is to be enclosed in said container. According to the invention the process consists of collecting the sample during the pouring of the material into the container using an apparatus fixed to the upper container rim and having a bucket below the liquid material stream and recovering the collected sample in the bucket.

Thus, the sample can be taken when the pouring speed is stabilized and linear.

The main application of such a process is for radioactive glass prior to its permanent confinement in a container. In this case, the apparatus used is permanently left in the container and is enclosed therein with the vitrified product.

A second main object of the invention is an apparatus for automatically collecting a material sample at least instantaneously in the liquid phase and poured into a container.

According to the invention, the apparatus comprises a bucket for collecting the material, an arm at whose end is fixed to the bucket, a support rod on which the arm is installed and mean fixing to the upper rim of the container of said support rod in such a way that the bucket can be located beneath the pouring stream and can collect the sample.

In the main embodiment of the invention, the arm is fitted so as to oscillate about a horizontal axis and a vertical axis and the apparatus comprises means for controlling and performing there two rotations of the arm. In this case, the first rotation of the arm about the vertical axis takes place from an initial position removed from the liquid material stream towards a sample removal position of the bucket below the liquid material stream. The second rotation of the arm around the vertical axis takes place from the sample removal position to a folded back position removed from the liquid material stream.

In the preferred embodiment of the control means, the latter are partly constituted by a fusible or meltable pellet on which rests a weighted rod blocking in its initial position the said arm and freeing it to permit rotation as a result of the dropping of the weighted rod during the melting of the pellet at a given temperature.

The initial horizontal rotation of the arm can be brought about in two different ways.

The first consists of using a prestressed helical spring fitted around the support rod, a first end being fixed to the rod, the second end being fixed to the arm, in order in this way to bring about the rotation of the arm about the vertical axis. The second consists of using a rotation counterweight in suspended form and horizontally connected to the arm by a cable passing over pulleys.

The rotation of the arm around the horizontal axis is preferably controlled by a counterweight placed at the second end of the arm in order to maintain in a high filling position the said bucket and in order to oscillate the arm when the bucket is full of liquid material and free the arm from an abutment fixed in rotation, which thus frees the rotation of the arm up to the folded back position.

The preferred bucket construction involves it having two superimposed compartments. Another main object of the invention is an apparatus for recovering the bucket containing the collected material following the cooling of the apparatus described hereinbefore. According to the invention this apparatus comprises means for positioning on the upper rim of the container and on which is installed a gripper having several claws maintained in the closed position by return springs, so as to permit them to assume two different vertical positions, namely an upper rest position, the claws being closed and a lower, gripping position, the claws then being open during the lowering of the gripper in order to seize the bucket by its upper rim.

These two apparatuses are advantageously completed by a third apparatus for bringing the arm of the apparatus for collecting the sample into its sample removal position prior to the recovery of the bucket and incorporating means for fixing on the upper rim of the container with an angular indexing and on which a first vertical drive rod is mounted so as to pivot with respect to a vertical axis, so that the oscillating arm of the apparatus for collecting the sample is made to rotate from its folded back position to its recovery position by the driving of the lower end of the first vertical drive rod on the upper end of a second vertical drive rod of the oscillating arm of the apparatus for collecting the sample.

All these three apparatuses are particularly suitable for removing a radioactive glass sample during its pouring into its storage container.

LIST OF DRAWINGS

The invention is described in greater detail hereinafter relative to non-limitative embodiments and the attached drawings, wherein show:

FIGS. 1A, 1B and 1C, in section, the apparatus for collecting the sample before, during and after the filling of its bucket in accordance with the invention.

FIG. 2, in partial section, a first embodiment of the apparatus for collecting the sample according to the invention.

FIG. 3, in partial section, a second embodiment of the apparatus for collecting the sample according to the invention.

FIGS. 4A and 4B, in section, the apparatus for bringing the arm of the apparatus of FIG. 3 into its sample removal position.

FIGS. 5 and 6, in section, the apparatus for collecting the sample according to the invention in the bucket of the apparatus according to FIG. 3 before and after said recovery.

DETAILED DESCRIPTION OF THE EMBODIMENTS OF THE INVENTION

Process According to the Invention

Figure 2:
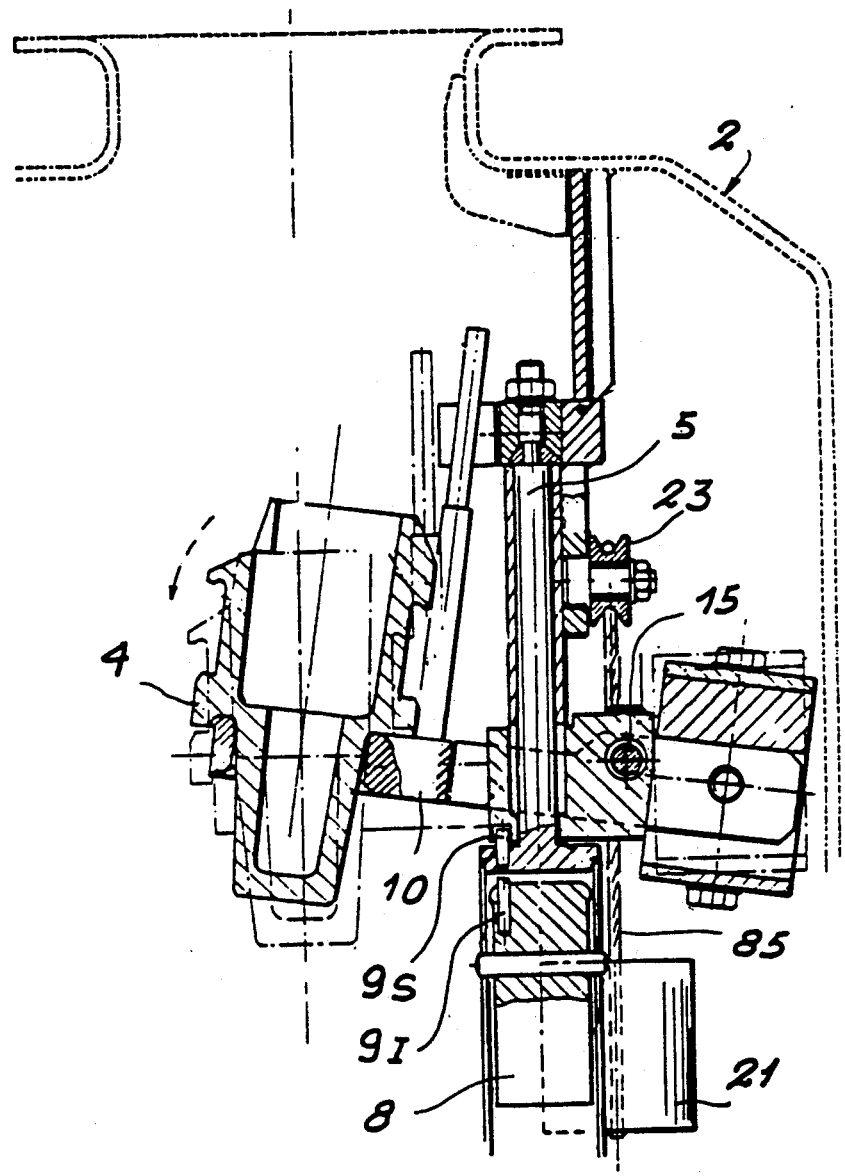

The inventive concept is based on the fact that it must be possible to remove samples, particularly of radioactive glass, on existing installations. The apparatuses according to the invention and described hereinafter are not manufactured at the same time as the container in or on which they are installed and certainly not at the same time as the glass melting furnace.

The first main phase of the process consists of removing the sample of glass during its pouring into its container. This clearly involves the process according to the invention being applicable to a material which, at the time of the filling of the container in which it is to be placed, is in liquid form. Particular consideration is given to radioactive glasses, which pass in liquid phase out of the melting furnace and which are directly poured into their storage container. To this end and with reference to FIGS. 1A, 1B and 1C, use is made of an apparatus fixed to the upper rim 3 of the container 2 into which the material is poured. This apparatus more particularly comprises a bucket 4, which will be brought below the material pouring stream 12.

The second main phase consists of recovering the sample collected in the bucket 4, preferably when the material has solidified. Two other apparatuses can then be used for carrying out this operation.

In the case of a radioactive product, the apparatus installed in the container beforehand for removing the sample is left there permanently and is enclosed therein with the vitrified product. This avoids the risk associated with the contamination of the equipment which has been in contact with the radioactive product.

In the case of a radioactive glass, the melting of the latter can take place at a temperature close to 900° C. It is then necessary to wait several hours to enable the glass to cool and solidify.

Apparatus for Collecting the Sample

With reference to FIG. 1A, the apparatus 1 essentially comprises means 6 for fixing the apparatus 1 to the upper rim 3 of the container 2, a vertical rod 5 fixed to said fixing means 6, an oscillating arm 10 carrying at a first end the bucket 4 and at the other end a counterweight 11, a protective sleeve within which is located a weighted rod 8 bearing on the meltable pellet 7 and a stud 9 for locking the oscillating shaft 10 in rotation.

According to this arrangement, prior to sample removal, the bucket 4 is in a position removed from the pouring stream 12. To this end, the oscillating arm 10 is mounted so as to rotate horizontally about the vertical rod 5. It can therefore assume an angularly displaced position with respect to the plane of the drawings. In order to make this position visible, the counterweight 11 is shown in perspective and the bucket 4 is not located below the pouring stream 12.

During the filling of the container 2, the fluid drops within the latter and the level of the liquid gradually rises. Bearing in mind the still high temperature of the liquid, the temperature within the container 2 rises and more particularly at a fixed point where the meltable pellet 7 is located. Thus, the latter is positioned at a point predetermined in such a way that it melts at the time at which it is wished to fill the bucket 4. Therefore its height in the container 2 is predetermined. This meltable pellet 7 constitutes an advantageous means for controlling the rotation of the oscillating arm 10 in order to place the bucket beneath the pouring stream 12.

Thus, with reference to FIG. 1B, the pellet 7 is shown in melted form, so that the weighted rod 8 has dropped, as a result of a hole 13 made in a cell 14 within which is placed the meltable pellet 7. Thus, there has also been a descent of the stud 9, which is integral with the weighted rod 8.

As can be seen in greater detail in FIG. 2, the stud 9 has an upper portion 9S inserted in the fixed rod 5 and the mobile oscillating arm 10. Its lower portion 9I is fixed in the weighted rod 8. Thus, when the latter descends by penetration in the hole 13 of the cell 14, the upper portion 9S is extracted from the oscillating arm 10 and the rod 5. The two latter members are then free to rotate and the arm 10 can rotate about the vertical axis of the rod 5. This rotation enables the bucket 4 to be positioned below the stream 12, so as to collect a predetermined liquid quantity.

In its preferred embodiment, the apparatus according to the invention also has means for controlling a second horizontal rotation from said sample removal position to a folded back position, once the bucket 4 has been filled. In this folded back position, the bucket 4 is removed from the pouring stream 12. An advantageous way for obtaining this second rotation consists of equipping the oscillating arm 10 with a counterweight 11 located opposite to the bucket 4. This counterweight essentially balances the liquid mass contained in the bucket 4. Thus, when the latter is filled, the oscillating arm 10, under the action of the weight of the sampled liquid tilts slightly about an axis perpendicular to the vertical axis. For this purpose, the oscillating arm 10 is also mounted so as to rotate about a horizontal shaft 15 mounted in a yoke 16 integral with the vertical rod 5. The counterweight 11 must be designed in such a way that this tilting takes place once the bucket 4 is filled with the liquid to be sampled.

This tilting of the oscillating arm 10 makes it possible to free an abutment 17 integral with the arm 10 from a slot 18 made in a stop member 19, which is fixed with respect to the vertical rod 5, i.e. with respect to the fixing means 6. This freeing action enables the oscillating arm 10 to perform the second horizontal rotation in order to remove the bucket 4 from the pouring stream 12. This operation is diagrammatically indicated in FIG. 1C, where the oscillating arm 10 is shown in the horizontal position, the bucket 4 being full.

FIG. 1C also indicates in dotted line form the second main phase of the process according to the invention, i.e. the removal of the bucket 4 from the container 2 and the extraction of the solidified glass sample 20 from the bucket 4.

The initial sample removal and filling positions of the bucket 4 are consequently obtained by horizontal rotations of the oscillating arm 10 about the vertical axis of the rod 5. The present description proposes two constructions for the means for rotating the oscillating arm 10 around the vertical rod 5.

With reference to FIG. 2, the first embodiment consists of using a rotation counterweight 21 suspended on a cable 85 passing round a pulley 23 fixed relative to the vertical rod 5. The not shown end of the cable 85 is fixed to the oscillating arm 10 or to a part integral with the latter, e.g. the yoke 16. The cable 85 is oriented with respect to the oscillating arm 10, so that the rotation counterweight 21 exerts a reaction on the oscillating arm 10, in off-centered manner with respect to the axis of the vertical rod 5. In this case, when the oscillating arm is freed from the stud 9 locking it in rotation in the initial position, the latter is subject to the pressure of the cable 85 and performs a rotation so as to position the bucket below the pouring stream 12. This position is determined by the position of the abutment 17 in the slot 18 of FIG. 3.

The rotation counterweight 21 acts in the same sense on the oscillating arm 10 in order to pass the bucket 4 from the sample removal position to the folded back position, when the arm 10 has been freed by the tilting of the stop member 19.

Figure 3:
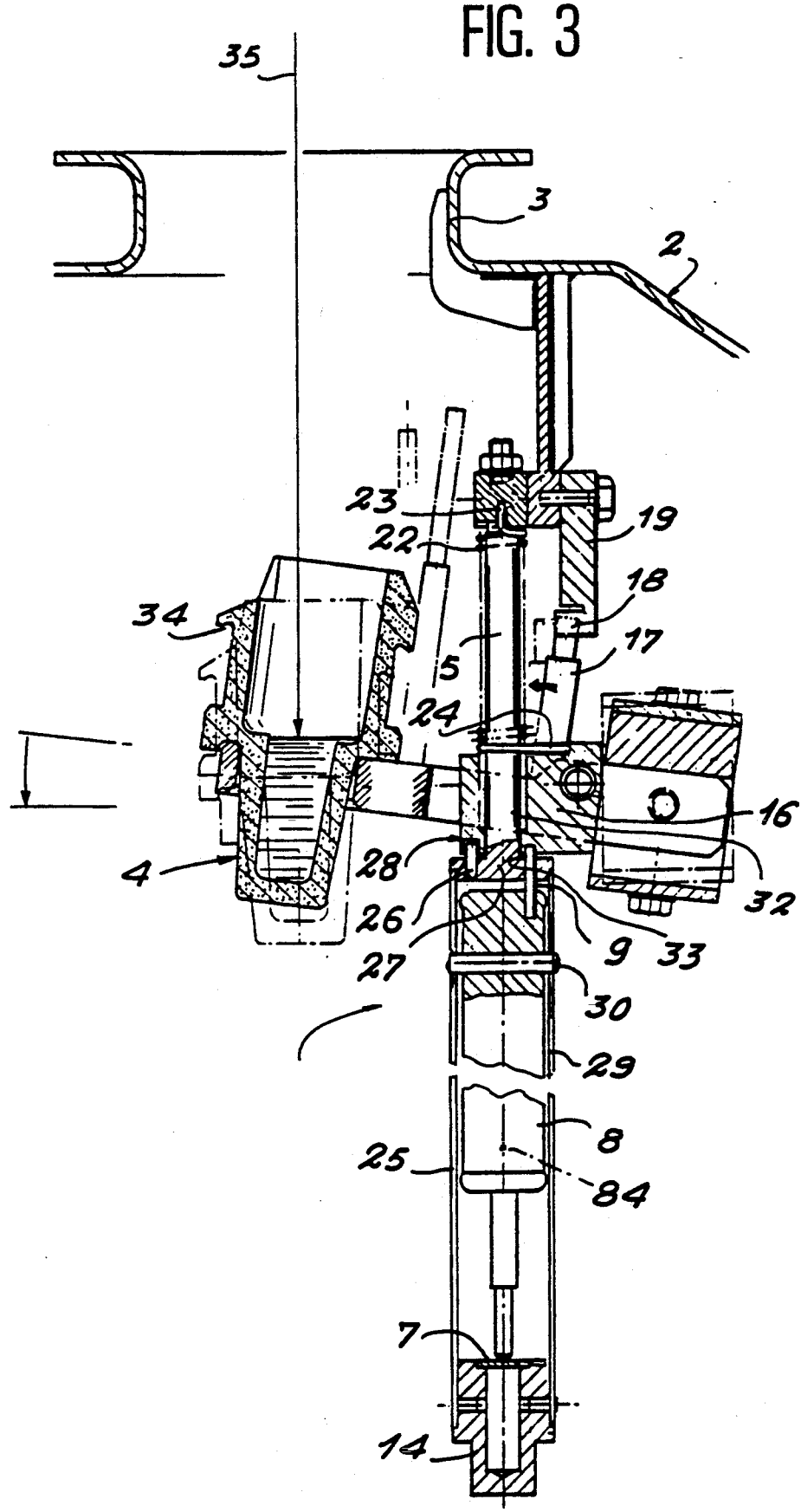

As shown in FIG. 3 and as suggested in FIGS. 1A, 1B and 1C, the second embodiment of the rotating means consists of using a helical spring 22 placed around the vertical rod 5. Its upper end 23 is fixed to the rod 5 or to the fixing means 6. The lower end 24 of the spring 22 is fixed to the oscillating arm 10. The spring 22 is prestressed in such a way that when the latter is free in rotation, the helical spring 22 tends to rotate the oscillating arm 10 in order to move it from its initial position to the sample removal position and then, when the oscillating arm 10 has tilted, to pass it from its sampling position to its folded back position.

The stud 9 is integral with the weighted rod 8 and traverses the base of the vertical rod 6 in order to penetrate the yoke 16 carrying the oscillating arm 10. Therefore the dropping of the weighted rod 8 ensures that the stud 9 is disengaged from said yoke 16. The latter is freed in rotation and can consequently turn with the oscillating arm 10. Moreover, a stop stud 26 is integral with the upper portion 27 of the sleeve 25 and penetrates a circular opening 28 made in the yoke 16. The circular opening corresponds to the angular travel or stroke between the initial rest position and the sample removal position. Thus, it is possible to stop the first rotation of the oscillating arm 10 in order to place the bucket 4 in its sample removal position.

The sleeve 25 is integral with the vertical rod 5 and maintains in place the cell 14 containing the meltable pellet 7. It also serves as a casing for the same and protects them from any product deposits due to the volatility of the liquid poured into the container. In its upper portion the sleeve 25 has two openings 29 for guiding the weighted rod 8, via a transverse pin 30 issuing into said openings 29. The function of the latter is to maintain the weighted rod 8 in its angular position during the raising of the weighted portion 8 in the sleeve 25.

Details concerning the use of the apparatus for collecting a radioactive glass sample during the pouring of said glass into its permanent storage container will now be described in a non-limitative manner. It is firstly pointed out that the apparatus can be used at a time when the pouring speed is approximately 400 kg of glass per hour.

This apparatus is entirely automatic, requires no human intervention and also no modification of the geometrical dimensions of the container. Thus, the first rotation of the oscillating arm 10 and the bucket 4 is controlled by the evolution of the temperature within the container 2. To this end, the meltable pellet 7 is placed at a very accurately predetermined height. With a pouring rate of 400 kg/hour, a 450 g bucket is filled in four seconds. Therefore the apparatus used responds very rapidly and in a perfectly reproducible manner.

The helical spring 22 used is preferably of the coil-type operating in torsion. It is wound up at the time of putting the apparatus into place. Its return or restoring force must be adequate to ensure the two horizontal rotations of the bucket 4 up to the folded back position. It should be noted that the spring 22 acts under thermal conditions such that it must withstand a temperature of 500° C. Consequently the material used for producing such a return spring can be Inconel 601. The spring 22 advantageously has 38 turns for a nominal diameter of 20 mm.

During the pouring of radioactive glass into a container 2 having an external diameter slightly smaller than 500 mm and a height exceeding 1 m, the latter is preheated at its base to 500° C. Therefore the material forming the meltable pellet 7 must meet certain criteria. The melting point must exceed the preheating temperature of the container 2. The melting point must be that of a pure element or a eutectic element or an alloy, which has a very restricted melting range. The design and material constituting the meltable pellet carrying cell 14 must be such that the heat exchange to the pellet 7 is aided so as not to bring about any melting delay. Therefore the cell 14 is made from the lightest possible material so as to only have a low heat load and its contacts with the meltable pellet are adequate. Bearing in mind these requirements, the pellet 7 is placed at 400 mm from the bottom and its melting point is 600° C. The material used can be an aluminium alloy $AG_3$, an aluminium—lithium alloy, silver-based hard solders, or zinc-copper or copper-tin alloys. It should be noted that the silver-based hard solder of the type Castellin 1802 manufactured by the Société Française Térotechnologique fully meets these operational requirements. The oscillating arm 10 can be of stainless steel.

The yoke 16 of the oscillating arm 10 can have a graphite bearing 32 in FIG. 3 and bears on a graphite ring 33 in order to facilitate the rotation around the vertical rod 5.

When radioactive glass melted in accordance with nuclear waste reprocessing standards is poured into a container, the surface temperature of the glass fluctuates between 800° and 900° C. Nevertheless the apparatus for collecting the sample must be positioned relatively close to the pouring nozzle which discharges the liquid glass, so as to ensure that the pouring stream is not moved away from the container by its angular displacement and so as to then facilitate the recovery of the bucket 4.

The ambient temperature at the apparatus must not be too high to limit the frictional forces, but must be adequate following the removal of the sample to ensure that the glass undergoes sufficiently slow cooling kinetics, particularly around and below the glass transition point. A cooling rate of approximately 75° C./hour from 5500° C. is acceptable for avoiding the fracturing of the sampled material. Bearing in mind the thermal radiation in the volume within the container 2 in the apparatus according to the invention, in the walls of the container 2 and in the bucket 4, the latter should be positioned at 925 mm from the bottom of the container 2.

In order to facilitate the reception and removal of the sampled material, the bucket 4 is provided with two superimposed compartments, the upper compartment having a larger diameter than the lower compartment.

In order to facilitate the future removal of the bucket 4 from the apparatus, a rim 34 is provided on the outside of the upper portion of the bucket 4. The bucket displacements take place over an angle of approximately 90°. The vertical rod 35, integral with the oscillating arm 10, will be used just prior to the removal of the bucket 4. The compartments of the bucket 4 have a slight vertical clearance in order to facilitate the removal of the solidified sample.

Apparatus for Bringing the Oscillating Arm into its Initial Position

FIG. 4B shows in plan view the upper opening of the container 2, within which is located the apparatus described hereinbefore. It is in particular possible to see the bucket 4 and the pivot pin 36 for the oscillating arm 10. The bucket 4 is in the folded back position, i.e. it is outside the opening of the container 4. With reference to FIGS. 4A and 4B, there is also an apparatus 40 for bringing the oscillating arm 10 into its sample removal position, following the filling cycle of the bucket 4, in order to recover the sample. It is essentially constituted by a rotary arm 46 pivoting about a vertical axis 44 and at one end of which is located a first vertical drive rod 41. This apparatus 40 is fixed to the upper rim of the container 2 using fixing means, which can be in the form of a body 42 fitting into the opening of the container 2. There is an angular indexing by means of indexing studs 99. Once the apparatus 40 has been fixed to the container 2, the lower end 47 of the first drive rod 41 is located against the upper end 48 of a second drive rod 43, which is integral with the oscillating arm 10.

A rotation of this apparatus about the vertical axis 44 leads to the rotation of the oscillating arm 10 around the vertical axis of the vertical rod 5. The apparatus incorporating the bucket 4 can consequently be displaced in such a way that the latter is again in its sample removal position. In the application to radioactive glass described hereinbefore, the displacement of such an apparatus exceeds 60°.

Figure 4:
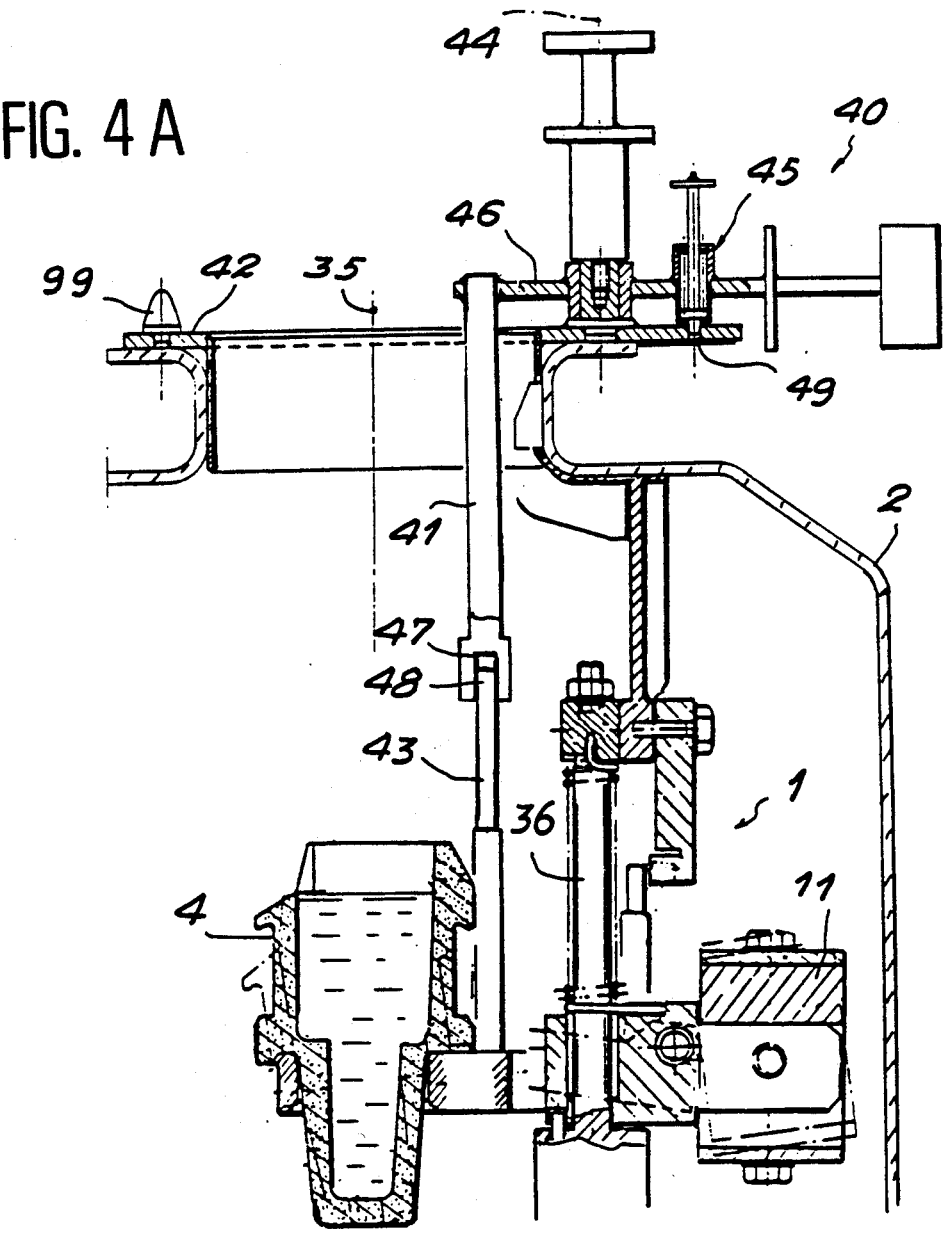
Figure 4:
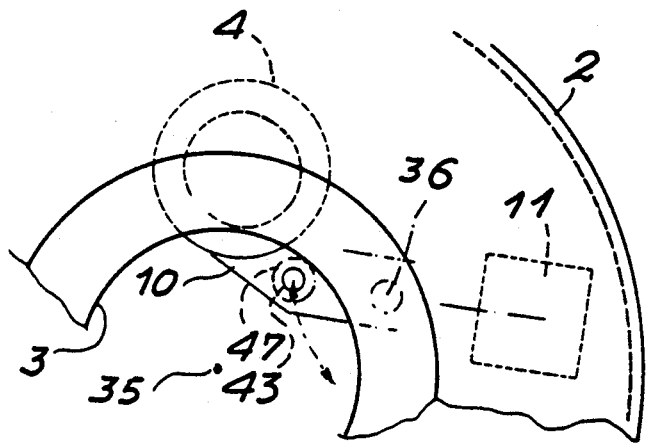

FIG. 4B also shows the second drive rod 43 placed on the oscillating arm 10. The angular travel of this arm 46 is limited by an abutment, which is symbolized in FIG. 4 by a spring abutment 45, whose end enters a hole 49 in the rim of the fixing cylinder 42. Once the bucket 4 has been returned to its sample removal position, the recovery of the sample by retracting the bucket 4 can take place.

Apparatus for Recovering the Bucket

Figure 5:
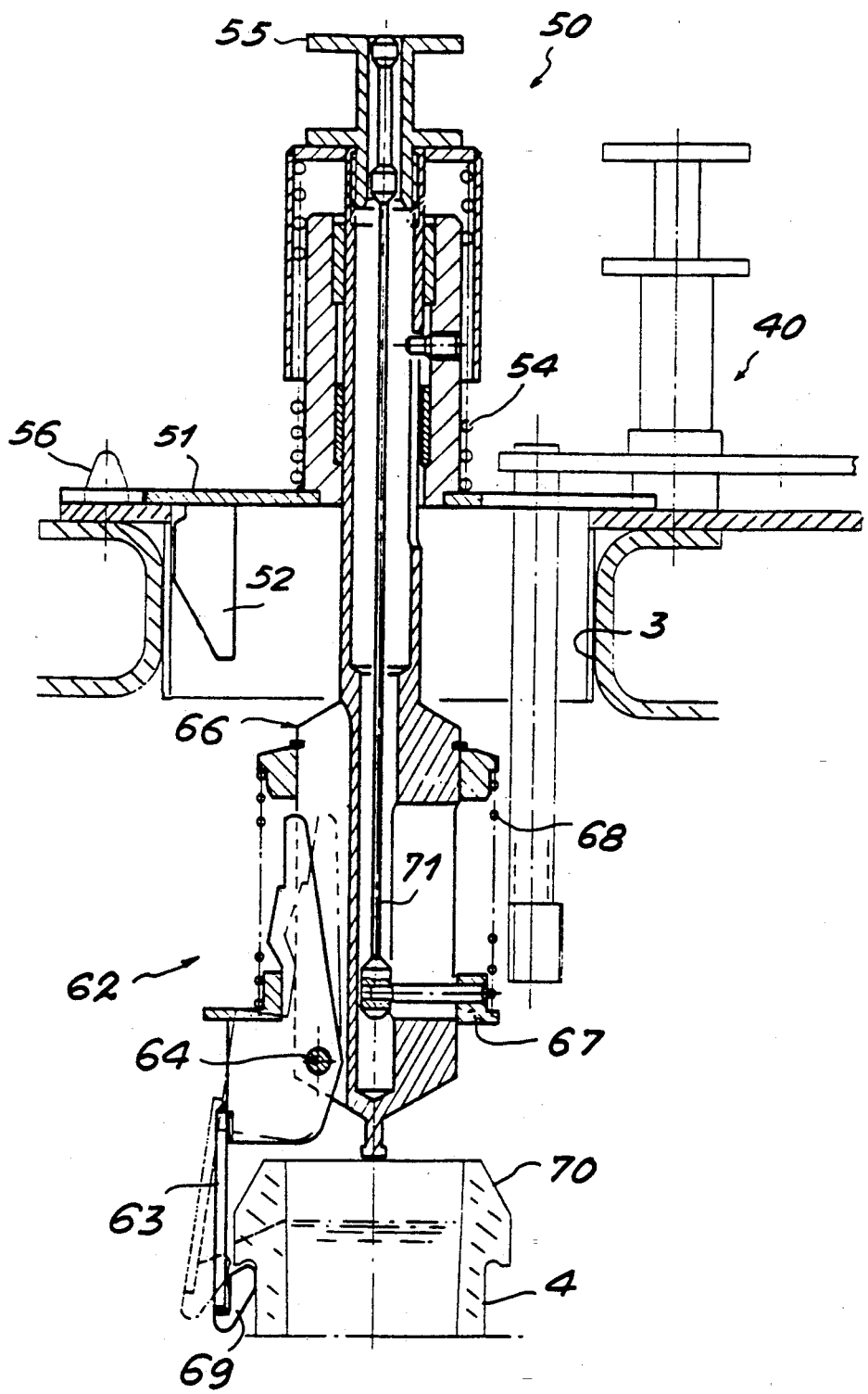

With reference to FIG. 5, the apparatus for recovering the bucket 4 essentially comprises fixing means on the container rim 3 and a gripper 62. The fixing means incorporate a horizontal plate 51 to which are vertically fixed centering flats 52. Centering studs 56 are also fixed to the horizontal plate 51.

The gripper 62 is constituted by several claws 63 mounted so as to pivot about horizontal axes 64 on a gripper body 66. The gripping of the bucket 4 takes place via the lower ends 69 of the claws 63, which are maintained in the closed position by not shown return springs.

The gripper 62 is maintained in the raised position by a return spring 54, which bears on the fixing plate 51 and which supports a handle 55 integral with the gripper 62. A ring 67 surrounds the claws 63 to keep them closed. In order to recover the bucket 4, a vertical pressure must be exerted on the handle 55 in order to lower the latter, together with the gripper 62. A machined ring 70 on the upper rim of the bucket 4 then moves apart the claws 63. The ring 67 rises by sliding along the claws. At the end of the descent, the claws close under the action of their respective return spring.

The body 66 of the gripper 62 is hollow and has a rod 71 integral with the ring 67. It has an indicator function by indicating, as a result of its displacement, that the claws 63 have closed correctly during the descent of the gripper 62. The displacement of the ring 67 is brought about by a second return spring 68 surrounding the body 66. The raising of the gripper 62 and the bucket take place by releasing the pressure on the handle 55.

In the case of radioactive glass, the gripper 62 is manipulated by a telemanipulator.

Figure 6:
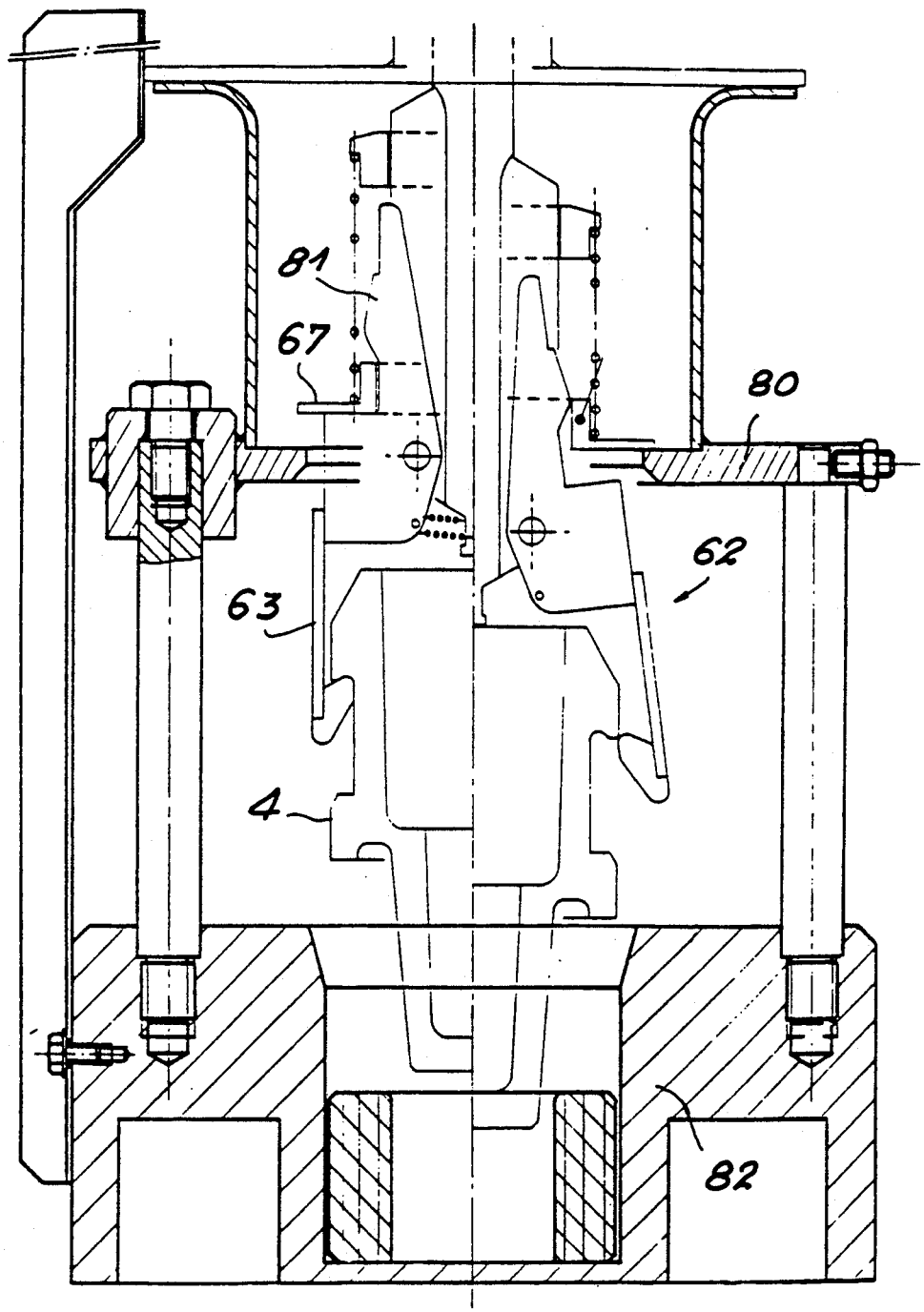

Once again, in an application to radioactive glass, it is also necessary to have a telemanipulator for releasing the bucket 4 from the gripper 62. With reference to FIG. 6, the assembly of the gripper 62 and the bucket 4 is placed on a support 80. A pressure on the handle 55 makes it possible to move apart the claws 63 by a slight raising of the ring 67 against the bosses 81 of the claws 63. It should be noted that the force necessary for bringing about this opening can be that of the weight of the assembly. Once freed, the bucket 4 drops into a bearing part 62. The gripper 62 is then raised with the aid of the telemanipulator.

The sample in the bucket 4 can be freed by turning over the assembly. The sample is then placed in an appropriate container with a view to its dispatch to the characterization department carrying out the analyses.

The apparatus for taking the sample with the aid of the bucket 4 is preferably only used once in the case of radioactive glass.

The process and apparatuses according to the invention make it possible to take radioactive glass samples directly in the storage container and without human intervention, when the system integrated into the furnace has not been provided. It therefore permits the recovery of glass samples in an appropriate form for analysis. Its control is automatically regulated by the thermal evolution of the pouring process.

It should be noted that the folded back position of the oscillating arm 10 makes it possible to obtain acceptable cooling kinematics for the sample.

We claim:

1. Apparatus for the automatic collecting of a material sample of a glass composition in its liquid phase while the glass composition is being poured as a liquid stream into an open container having an upper rim and with said glass composition solidifying in said open container, comprising:
    a bucket for collecting the material sample,
    a support rod extending from said upper rim of said container in substantial vertical alignment with the longitudinal axis of said container;
    an oscillating arm connected to said bucket and rotatably mounted on said support rod for rotation about said support rod in such manner so as to reciprocate said bucket into a position beneath said liquid stream and for retracting said bucket from said position; and
    means for controlling the rotation and retraction of said oscillating arm, so that said bucket can collect said sample while the bucket is beneath the liquid stream.

2. Apparatus according to claim 1, wherein said oscillating arm is mounted so as to oscillate about a horizontal axis and a vertical axis of said support rod and further comprising means for permitting a first rotation of said oscillating arm about said vertical axis from an initially retracted position with said bucket removed from said liquid stream to a position with said bucket positioned beneath said liquid stream and for permitting a second rotation of said oscillating arm about the vertical axis to retract said bucket from said sample removal position to a folded back position removed from said liquid stream.

3. Apparatus according to claim 1, wherein the shape of said bucket is such that said bucket has two volumes.

4. Apparatus according to claim 1, wherein the glass composition is radioactive glass which is being poured into a permanent storage container.

5. Apparatus for the automatic collecting of a material sample of a glass composition while in its liquid phase while the glass composition is being poured as a liquid stream into a container having an upper rim with said liquid stream solidifying in said container, comprising:
    a bucket for collecting the material samples,
    an oscillating arm connected at a first end thereof to said bucket,
    a support rod on which said oscillating arm is mounted, with said support rod extending from said upper rim of said container, so that said oscillating arm can reciprocate said bucket into a position beneath said stream for collecting the sample;

said oscillating arm being mounted so as to oscillate about a horizontal axis and a vertical axis of said support rod with said apparatus further comprising; means for controllably rotating said oscillating arm about the vertical axis of said support rod from an initially retracted position with said bucket removed from said liquid stream to a position with said bucket positioned beneath said liquid stream and for rotatably retracting said oscillating arm to a folded back position removed from said liquid stream; and further comprising a meltable pellet for maintaining the arm in said initially retracted position and for freeing the arm for rotation upon the melting of said pellet.

6. Apparatus according to claim 5, wherein said means for rotating said oscillating arm comprises a prestressed spring mounted around said vertical support rod and having a first upper end fixed to said support rod and a second lower end fixed to said oscillating arm so as to permit said oscillating arm to rotate about said vertical axis of said support rod.

7. Apparatus according to claim 5, wherein said means for controllably rotating said oscillating arm comprises a counterweight connected by means of pulleys and a cable to said oscillating arm.

8. Apparatus for the automatic collecting of a material sample of a glass composition in its liquid phase while the glass composition is being poured as a liquid stream into an open container having an upper rim and with the glass composition solidifying in said open container, comprising:

a bucket for collecting the material sample, a support rod extending from said upper rim of said container in substantial vertical alignment with the longitudinal axis of said container;

an oscillating arm connected to said bucket and rotatably mounted on said support rod for rotation about said support rod in such manner so as to reciprocate said bucket into a position beneath said liquid stream and for rotatably retracting said bucket from said position; and means for controlling the rotation of said oscillating arm, so that said bucket can collect said sample;

wherein said oscillating arm is mounted so as to oscillate about a horizontal axis and a vertical axis of said support rod and wherein said apparatus further comprises means for permitting a first rotation of said oscillating arm about the vertical axis of said support rod from an initially retracted position with said bucket removed from said liquid stream to a position with said bucket positioned beneath said liquid stream and for rotatably retracting the oscillating arm about the vertical axis of said rod to a folded back position removed from said liquid stream;

wherein said means for controllably rotating said oscillating arm comprises a counterweight connected to said oscillating arm to free said oscillating arm for rotation when said bucket is filled with liquid material thus allowing said oscillating arm to rotate to the folded back position.

* * * * *